United States Patent
Dennison et al.

(10) Patent No.: US 8,317,723 B2
(45) Date of Patent: Nov. 27, 2012

(54) PRESSURE SENSOR FOR BIOLOGICAL FLUIDS AND USE THEREOF

(75) Inventors: Christopher Raymond Dennison, Victoria (CA); Peter Martin Wild, Victoria (CA); David Robert Wilson, Victoria (CA); Peter A. Cripton, Vancouver (CA); Marcel Dvorak, Victoria (CA)

(73) Assignee: UVic Industry Partnerships Inc., Victoria, B.C. (CA)

( * ) Notice: Subject to any disclaimer, the term of this patent is extended or adjusted under 35 U.S.C. 154(b) by 693 days.

(21) Appl. No.: 12/280,148

(22) PCT Filed: Feb. 22, 2007

(86) PCT No.: PCT/CA2007/000286
§ 371 (c)(1),
(2), (4) Date: May 22, 2009

(87) PCT Pub. No.: WO2007/095752
PCT Pub. Date: Aug. 30, 2007

(65) Prior Publication Data
US 2009/0247899 A1    Oct. 1, 2009

Related U.S. Application Data

(60) Provisional application No. 60/776,600, filed on Feb. 23, 2006.

(51) Int. Cl.
*A61B 5/00* (2006.01)

(52) U.S. Cl. ..................................... 600/561

(58) Field of Classification Search .................. 600/587, 600/594, 365; 422/82.06, 82.07, 82.11; 73/705, 73/250; 324/96; 264/1.24, 157, 328.2; 385/10, 385/37, 27, 12, 13; 436/133, 136, 163, 68; 356/409, 410, 411
See application file for complete search history.

(56) References Cited

U.S. PATENT DOCUMENTS

| | | | |
|---|---|---|---|
| 5,124,130 A * | 6/1992 | Costello et al. ............ | 422/82.06 |
| 6,854,327 B2 * | 2/2005 | Rambow et al. ................ | 73/250 |
| 2002/0041724 A1 | 4/2002 | Ronnekleiv et al. | |
| 2003/0227097 A1 * | 12/2003 | Girardon et al. ............. | 264/1.24 |
| 2004/0129083 A1 * | 7/2004 | Fernald et al. .................. | 73/705 |
| 2006/0011820 A1 | 1/2006 | Chow-Shing et al. | |

FOREIGN PATENT DOCUMENTS

| CA | 2 353 452 A1 | 6/2000 |
|---|---|---|
| CA | 2 353 567 A1 | 6/2000 |

OTHER PUBLICATIONS

Smith, A., International Search Report for International Application No. PCT/CA2007/000286; Jun. 6, 2007.

* cited by examiner

*Primary Examiner* — Brian Szmal
(74) *Attorney, Agent, or Firm* — Klarquist Sparkman, LLP (57) ABSTRACT

A pressure sensor for connecting to a detector is provided. The pressure sensor comprises: an optical fibre, having a distal end with a distal plane for sensing pressure, a proximal end for communicating with a patch cord, and an In-fibre Bragg grating (FBG) therebetween; a housing, having a distal aperture, a proximal aperture and a bore therebetween, and sized to accept the optical fibre; an annular ring, forming a flexible seal between said optical fibre and housing at least distal to the FBG and a holder for retaining the housing. The FBG is housed in the housing such that in use, axial strain is transferred to said In-fibre Bragg grating housed within said housing by pressure exerted on the distal plane.

21 Claims, 11 Drawing Sheets

PRESSURE SENSOR FOR BIOLOGICAL FLUIDS AND USE THEREOF

CROSS REFERENCE TO RELATED APPLICATIONS

This is the U.S. National Stage of International Application No. PCT/CA2007/000286, filed Feb. 22, 2007, which in turn claims the benefit of U.S. Provisional Application No. 60/776,600, filed Feb. 23, 2006.

FIELD

The present technology relates to a pressure sensor for measuring fluid pressure in biological systems. More specifically the technology relates to a sensor employing In-fibre Bragg gratings.

BACKGROUND

Pressure sensors can be constructed using a number of technologies. One technology that has been used extensively is strain gauge technology. While strain gauges provide reproducible results under many conditions, they are not well suited to measuring pressure in biological systems. This is because of their relatively large size (2.5 mm diameter would be considered to be a very small strain gauge), the fact that they are electrical and therefore susceptible to malfunction in wet or conductive tissues, their poor resolution and susceptibility to electromagnetic interference.

In-fibre Bragg gratings (FBGs) are optical sensors that have been successfully applied in structural monitoring of various civil, and aeronautical structures. Although they are a proven alternative to conventional electronic sensors, they have not enjoyed widespread use. Several factors contribute to their limited application including cost and a lack of familiarity with optical technologies to users of traditional strain measurement systems.

FBGs have many qualities that are desirable in sensing applications. They are extremely small, with 50 μm outside diameter and sensor gauge lengths as short as a few millimeters. They require only one optical lead for illumination and data acquisition, as opposed to electronic strain gauges which require two leads. They are also unaffected by external electromagnetic fields, making shielding unnecessary. Further to this, because FBGs are non-metallic, they can be used within a magnetic resonance imaging scanner. The mechanical properties of FBGs are similar to those of silica glass, but their small size, especially in relation to their diameter makes them flexible. Therefore they can be bent and twisted to accommodate their host structure. They minimally impact the mechanics of the host structure because of their small size. Despite this, FBGs have not been used extensively in medical and biomedical applications.

One example of a medical application is disclosed in US patent publication number 20020041724. Disclosed is a body compatible fiber optic sensor probe for invasive medical use that includes an optical fiber, a sensing location at which the fiber is configured to provide at least one detectable changeable optical property responsive to a strain within the fiber, and at least one sensing element which undergoes a volumetric change in response to an in body parameter to be sensed. The sensing element is coupled to the fiber in such a way that the volumetric change induces the strain within the fiber so as to vary the detectable changeable optical property. In the preferred embodiment, a FBG is used and a thick polymer coating such as a hydrogel is the sensing element. The polymer coating on the fibre causes the fibre to strain more, when exposed to pressure on its outer cylindrical surface, than if the fibre itself were exposed to the pressure. The pressure is not localized and therefore a relatively large sample volume is needed. Hence, the invention would not be suitable for measuring pressure in confined body spaces, such as intervertebral discs. Further, the use of a polymer that can absorb water could introduce errors in measurements.

It is an object of the present technology to overcome the deficiencies in the prior art.

SUMMARY

A pressure sensor for connecting to a detector is provided. The pressure sensor comprises; an optical fibre, having a distal end with a distal plane for sensing pressure, a proximal end for communicating with a patch cord, and an in-fibre Bragg grating (FBG) therebetween; a housing, having a distal aperture, a proximal aperture and a bore therebetween, and sized to accept the optical fibre and in-fibre Bragg grating; an annular ring, forming a flexible seal between said optical fibre and housing at least distal to the FBG and a holder for retaining the housing. The FBG is housed in the housing such that in use, axial strain is transferred to said in-fibre Bragg grating housed within said housing by pressure exerted on the distal plane.

In one aspect, the housing is bio-medical tubing.

In another aspect, the housing is at least about 0.051 mm inside diameter and is at most about 2 mm inside diameter.

In another aspect, the housing is at least about 0.2 mm inside diameter and is at most about 1.6 mm inside diameter.

In another aspect, the housing is 0.2 mm inside diameter.

In another aspect, the housing is selected to limit pressures on the FBG to axial pressures.

In another aspect, the FBG is 0.125 mm outside diameter and the housing is 0.2 mm inside diameter.

In another aspect, the FBG is 10 mm in length.

In another aspect, the housing is a glass tube or a hypodermic tube.

In another aspect, the annular ring comprises silicone sealant.

In another aspect, the optical fibre and the housing are essentially co-terminus at a distal end.

In one aspect a method is provided for measuring fluid pressure in a sample comprising inserting the pressure sensor into the sample, measuring an optical response, and comparing the optical response with a standard curve thereby measuring fluid pressure.

In another aspect, the method further comprises the step of calibrating the pressure sensor.

In another aspect of the method, the sample is a bio-medical sample.

In another aspect of the method, the bio-medical sample is studied to assess at least one of intervertebral discs pressure, cartilage pressure, fluid pressure within a trabecular bone, lumbar instability, spinal cord injury, spinal stenosis, disc degeneration, or to conduct provocative discography.

In another aspect of the method the bio-medical sample is an intervertebral disc.

In one aspect, a method of manufacturing a bio-medical pressure sensor is provided comprising the steps of selecting a biocompatible housing, the housing having a distal aperture, a proximal aperture and a bore therebetween, inserting an optical fibre comprising a FBG into the housing such that the FBG is within the housing, sealing the optical fibre to the biocompatible housing with a flexible annular ring at least distal to the FBG and inserting the housing into a holder to retain the housing and the optical fibre therein, thereby manufacturing a bio-medical pressure sensor.

In another aspect of the method of manufacturing, the housing is bio-medical tubing.

In another aspect of the method of manufacturing the housing is at least about 0.150 mm inside diameter and is at most about 2 mm inside diameter.

In another aspect of the method of manufacturing the housing is at least about 0.2 mm inside diameter and is at most about 1.6 mm inside diameter.

In another aspect of the method of manufacturing the housing is 0.2 mm inside diameter.

In another aspect of the method of manufacturing the housing is sized to accept the optical fibre and to limit pressures on the FBG to axial pressures.

In another aspect of the method of manufacturing the FBG is 0.125 mm outside diameter and the housing is 0.2 mm inside diameter.

In another aspect of the method of manufacturing the FBG is 10 mm in length.

In another aspect of the method of manufacturing the housing is a glass tube or a hypodermic tube.

In another aspect of the method of manufacturing the annular ring comprises silicone sealant.

In another aspect of the method of manufacturing the optical fibre and the housing are essentially co-terminus at a distal end.

In another aspect, the sensor further comprises at least two FBGs therebetween.

DETAILED DESCRIPTION

Example 1

Experiments were conducted to explore the feasibility of using FBG sensors to measure spinal disc pressure in human lumbar spines. To assess the ability of FBGs to measure disc pressure a first embodiment of the technology was developed. An ST sensor was used as a control.

Figure 1:
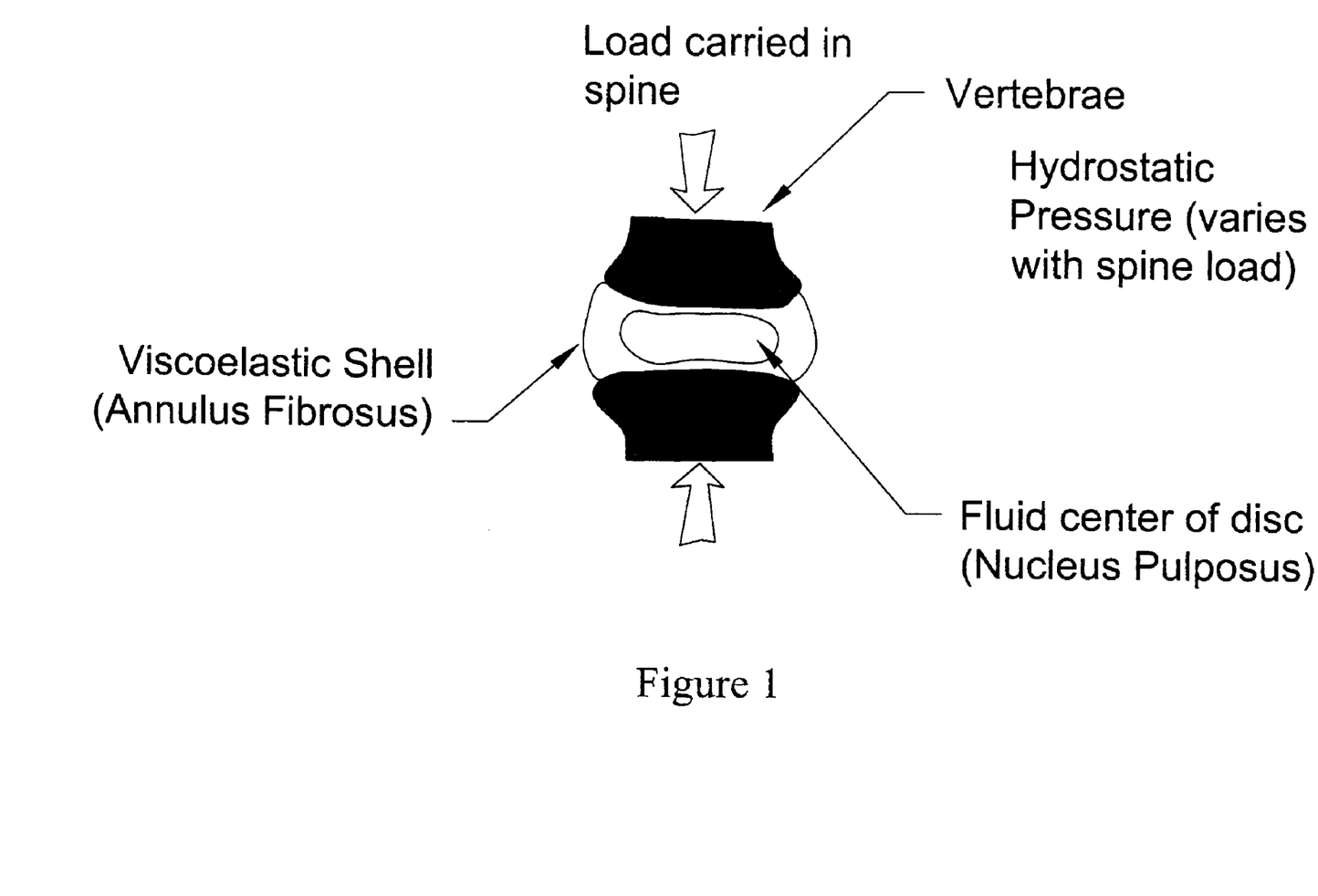
FIG. 1 is a schematic cross section of an intervertebral disc.

The discs of a human spine consist of two regions. The first region is the annulus. The tissue of the annulus is soft and pliable, but it also offers significant resistance to applied loads. The nucleus pulposus (NP) is at the center of the annulus and is a viscous liquid. FIG. 1 is a schematic cross section of the disc.

Experimental Design

Figure 2:
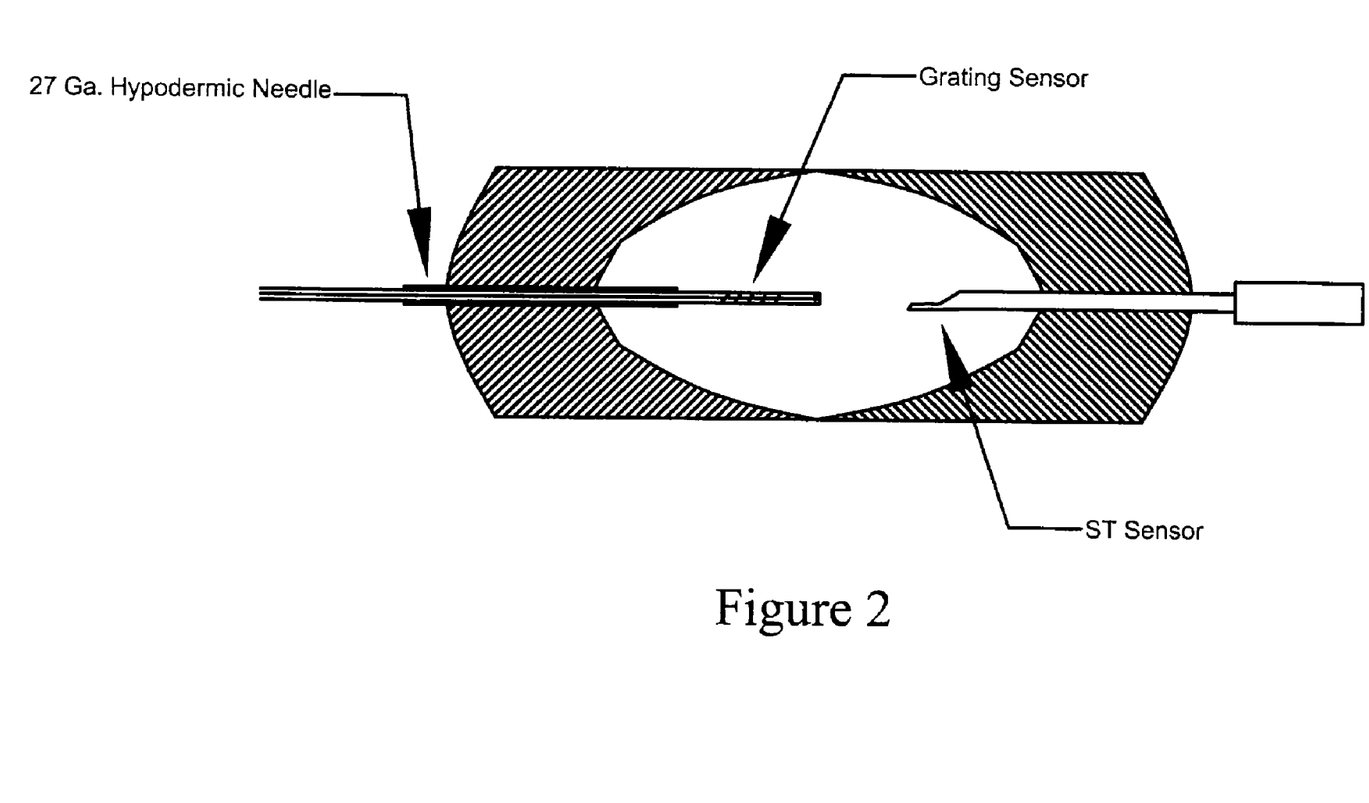
FIG. 2 is a schematic showing both a FBG and a strain gauge transducer (ST) inserted into the disc for measuring pressure.

FIG. 2 is a schematic showing both a FBG of a first embodiment and an ST sensor installed in a human disc. To preserve the mechanics of the spine, the vertebrae on the top and bottom of the disc were left attached. To allow loading of the disc, the disc fixture was mounted into an Instron™ (materials testing) machine. The Instron applied and recorded spine load during the testing.

A 27. ga hypodermic needle was used to first pierce the disc; the needle was then advanced further into the disc until the tip of the needle reached the inner disc, which can be fluid, semi-fluid or even gelatinous.

The inside diameter of the hypodermic needle was large enough to allow a FBG sensor to pass through it. The FBG sensor was therefore inserted into the hypodermic needle, and advanced through the needle and into the nucleus of the disc. Once resistance was met, the location of the FBG sensor within the disc was noted by marking (on the FBG sensor patch-cord) the location of the FBG sensor relative to the end of the hypodermic needle left protruding from the annulus. The resistance was assumed to be the effect of the inner wall of the annulus on the opposite side of the disc. Therefore, the mark on the patch-cord at this location denoted the location of the annular wall of the disc. The FBG sensor could then be retracted from the zero location, and the new FBG sensor location would be marked on the patch-cord.

The location of the hypodermic needle in the disc was controlled. A reference mark on the outside of the needle was used as a depth gage for needle insertion. By inserting the needle up to this reference mark, and checking that the needle had not moved after each experiment, errors associated with needle translation within the disc were avoided.

With the FBG sensor installed as shown in FIG. 2, the disc was incrementally loaded from 0 to 2000N. The angular alignment of the top and base of the fixture were noted, and steps were taken to ensure the loads were purely compressive on the disc (spine-unit). After the fixture was adjusted to attain pure compression, the applied loads were increased and testing began. The Instron was set to apply load at a constant rate of 10 N/s from 0 to 2000 N, then hold at 2000 N for 15 s, and finally from 2000 to 0 N at 10 N/s. The Bragg Wavelength was recorded from the Optical Spectrum Analyzer (OSA) at regular intervals of 200 N.

Pressure data from the ST sensor were recorded in real time using software developed in LabView™. The procedures listed above were repeated four times on the same spine disc.

Results

Figure 3:
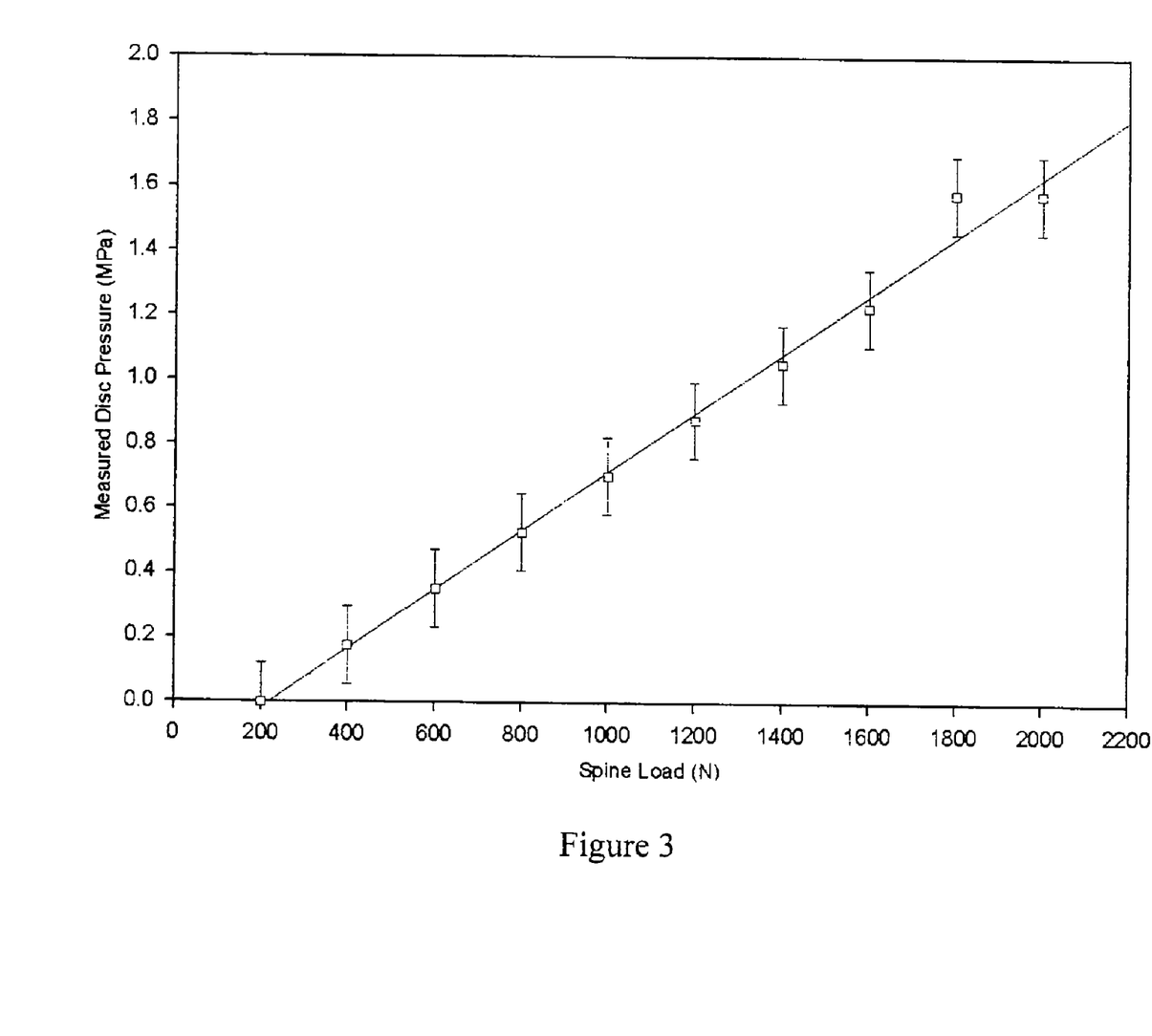
FIG. 3 shows the measured pressure versus applied load using the first embodiment in an intervertebral disc.

The results of a typical load test of an intervertebral disc are shown in FIG. 3. The observed linear pressure response to spine load is consistent with previous studies using different sensors. These results suggest that the FBG sensors are sufficiently linear to make clinically relevant measurements of disc pressure.

Example 2

Figure 4:
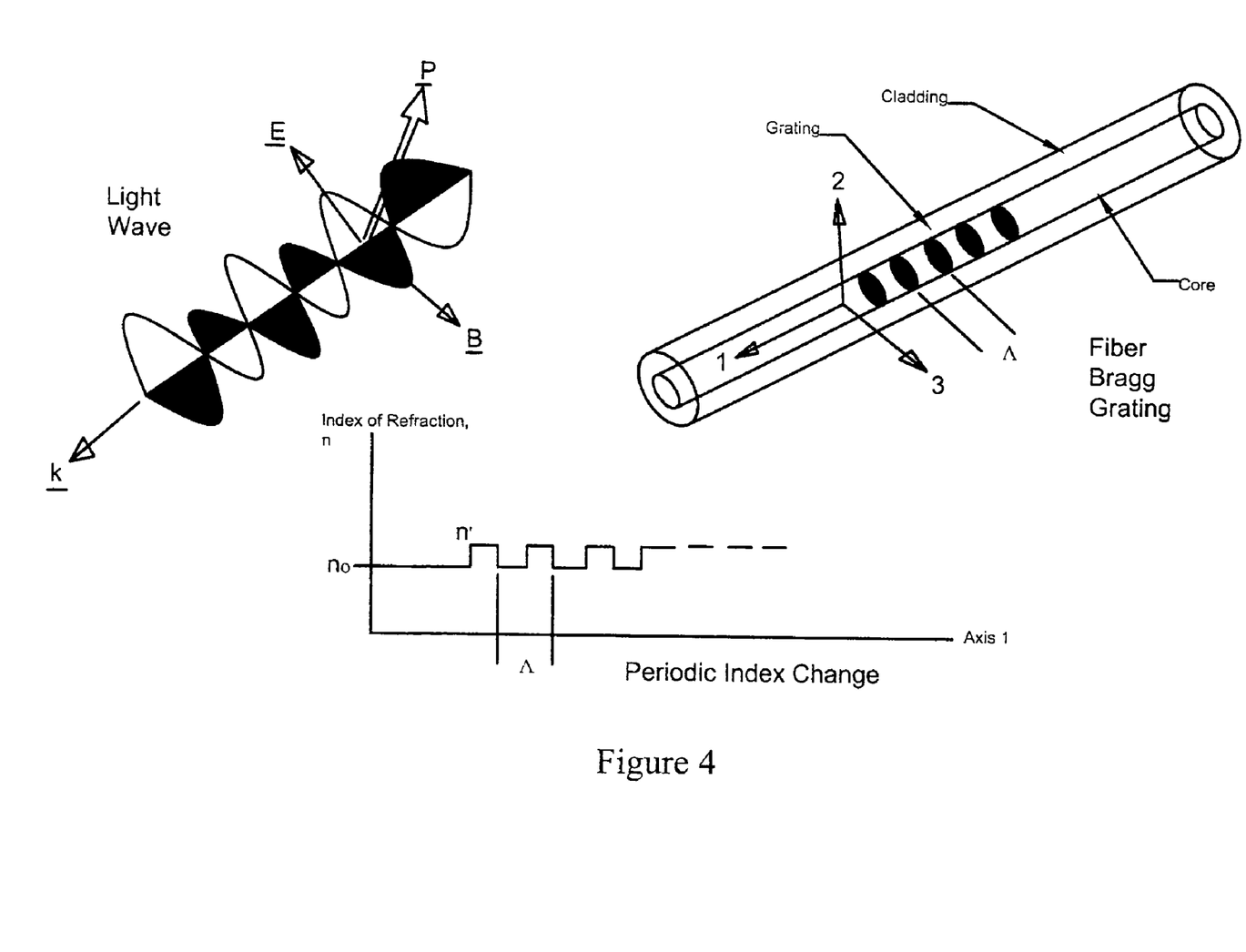
FIG. 4 shows a model of a FBG using plane electromagnetic waves including coordinate axis conventions.

A mathematical approach was taken to determine how to improve the sensitivity of the sensor. The derivation that follows is a general method that uses only two fundamental relations, Bragg's Condition and Nye's Equation for Photo-Elasticity for calculating FBG sensitivity. The light wave in FIG. 4 is a simple electromagnetic plane wave where the electric field, E, is orthogonal to the magnetic field, B. The wave propagates in a direction given by the wave vector, k. Although the light waves used to illuminate FBGs are not plane electromagnetic waves, we can still use this as a model. Typically, uni-axial FBGs such as those considered here are illuminated by elliptically polarized light. However, even with elliptically polarized light, the polarization vector, P, will always lie in the 2-3 plane shown on the FBG of FIG. 4. This allows the light wave depicted to be considered a snapshot in time of the elliptic light.

Bragg's Condition for FBGs is a simple relation that allows the calculation of the Bragg Wavelength reflected by the FBG:

$$\lambda_B = 2\Lambda n_0 \qquad (1.1)$$

Where $\lambda_B$ is the Bragg Wavelength, $\Lambda$ is the spatial period of the index of refraction profile, and $n_0$ is the nominal index of refraction for the core material. The second and final relation needed was proven by Nye in 1954:

$$\frac{\Delta n_i}{n_i} = -\frac{n_i^2}{2} p_{ij} \varepsilon_j \qquad (1.2)$$

Where $n_i$ are the indices of refraction for the co-ordinate system shown on the FBG in FIG. 4. The constants $p_{ij}$ are photo-elastic constants and are given in the tensor below. The strains are $\varepsilon_j$, and also follow the co-ordinate system on the FBG.

$$\left[\frac{\Delta \lambda_B}{\lambda_B}\right]_i = \frac{\Delta(2\Lambda n_i)}{2\Lambda n_i} = \frac{\Delta(\Lambda n_i)}{\Lambda n_i} = \frac{1}{\Lambda n_i}[(\Delta \Lambda)n_i + (\Delta n_i)\Lambda] = \frac{\Delta \Lambda}{\Lambda} + \frac{\Delta n_i}{n_i} \qquad (1.3)$$

Note that the tensor is symmetric and has only two independent quantities, $p_{11}$ and $p_{12}$.

The first step in calculating the sensitivity to a physical parameter is to take the normalized increment of (1.1).

$$\left[\frac{\Delta \lambda_B}{\lambda_B}\right]_i = \varepsilon_1 - \frac{n_i^2}{2} p_{ij} \varepsilon_j \qquad (1.4)$$

Again, the index i refers to the co-ordinate axes. The term $\Delta \Lambda/\Lambda$ is the axial strain along the 1-axis of the FBG, and $\Delta n/n_i$ is given in (1.2). With the above substitutions, a general relation results that can later be adapted to solve for an FBGs sensitivity to external system parameters.

$$p_{ij} = \begin{pmatrix} p_{11} & p_{12} & p_{12} \\ p_{12} & p_{11} & p_{12} \\ p_{12} & p_{12} & p_{11} \end{pmatrix} \qquad (1.5)$$

Figure 5:
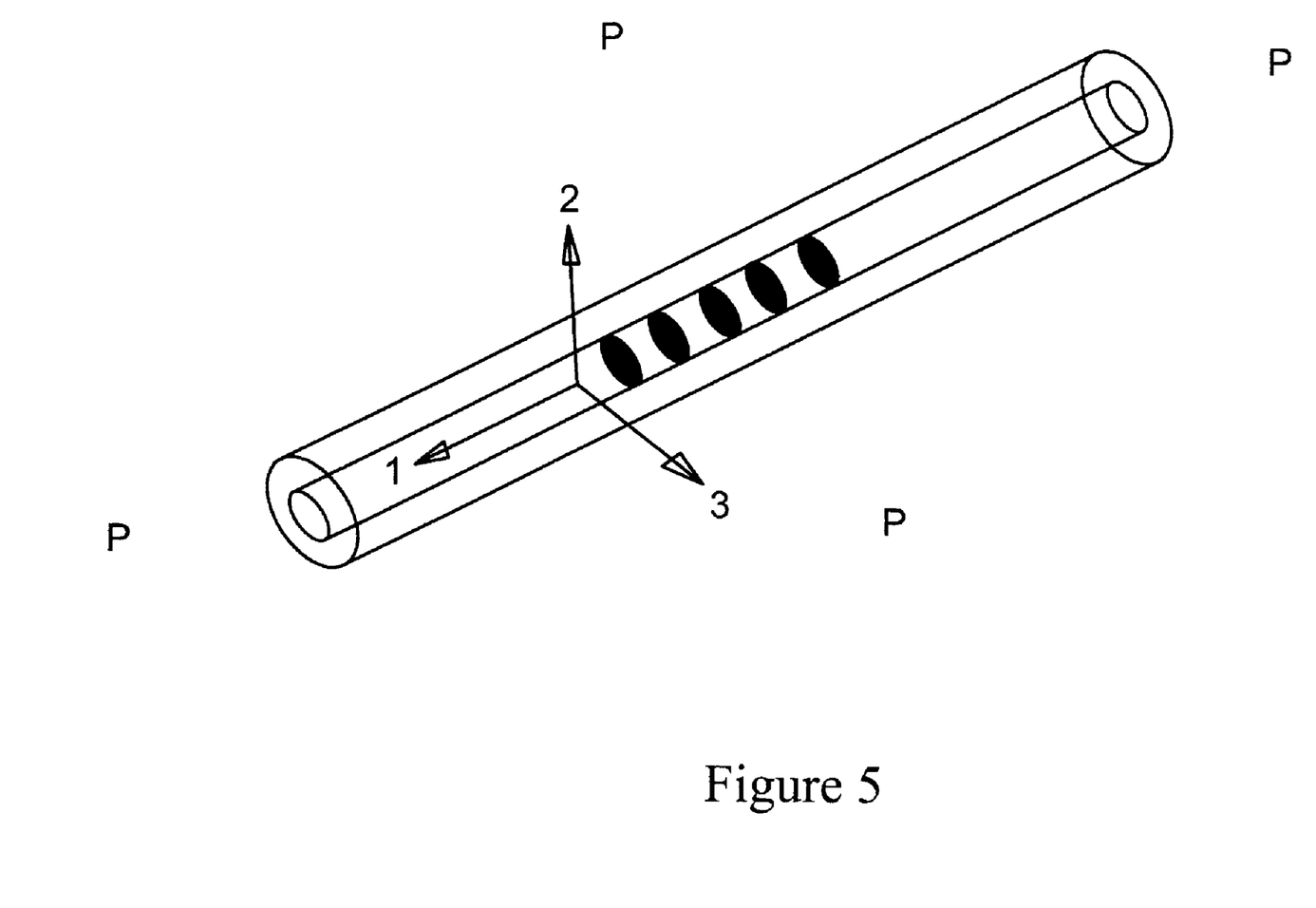
FIG. 5 shows the typical uni-axial FBG in a three-dimensional hydrostatic pressure field.

When a FBG is subjected to hydrostatic pressure, physical changes in the grating period are caused by the axial strains induced. FIG. 5 shows the typical uni-axial FBG in a three-dimensional hydrostatic pressure field. This Figure outlines the pressure boundary conditions of a first embodiment of the FBG sensor. FIG. 3 shows the measured pressure of the disc as reported by both the FBG and ST sensors from four trials.

To arrive at the curves presented in FIG. 3, the experimentally obtained FBG sensor sensitivity to pressure was used. The software used with the ST sensor reports pressure directly. Both the FBG and ST sensors responded linearly to applied spine load.

The three dimensional strain vector has three equal entries as a result of the isotropic stress field in the FBG.

$$\left[\frac{\Delta \lambda_B}{\lambda_B}\right]_2 = \frac{-P(1-2\nu)}{E} - \frac{n_{20}^2}{2}\left(\frac{-P(1-2\nu)}{E}\right)[2p_{12} + p_{11}] \qquad (1.6)$$

Where P is the change in external pressure, E is the Young's Modulus of the core, and $\nu$ is the Poisson ratio. If one substitutes (1.6) into (1.5) the following results:

$$\left[\frac{\Delta \lambda_B}{\lambda_B}\right]_2 = \frac{-P(1-2\nu)}{E}\left[1 - \frac{n_{20}^2}{2}[p_{11} + 2p_{12}]\right] \qquad (1.7)$$

Notice that (1.7) can be simplified further because the strain field is isotropic. Factoring the axial strain terms gives (1.8).

$$\left[\frac{\Delta \lambda_B}{P}\right]_2 = \frac{-\lambda_B(1-2\nu)}{E}\left[1 - \frac{n_{20}^2}{2}[p_{11} + 2p_{12}]\right] \qquad (1.8)$$

Re-arranging (1.8) to give the sensitivity to three dimensional hydrostatic pressure gives (1.9).

$$\varepsilon_j = \begin{bmatrix} 1 \\ 1 \\ 1 \end{bmatrix} \frac{-P(1-2\nu)}{E} \qquad (1.9)$$

Finally the subscripts 2, are dropped on the left hand side of (1.9) and also for $n_{20}$. The reason for this simplification is related to the elliptic nature of the light traveling along the axis of the FBG, that is, the light wave does not only occupy the axis 2, but the entire plane of axes 2-3. Therefore, the sensitivity to hydrostatic pressure is (1.10).

$$\left[\frac{\Delta \lambda_B}{P}\right] = \frac{-\lambda_B(1-2\nu)}{E}\left[1 - \frac{n_0^2}{2}[p_{11} + 2p_{12}]\right] \qquad (1.10)$$

Given knowledge of the FBGs material properties, one can now accurately measure pressure changes given that the change in Bragg wavelength is known. Substituting typical material properties for the FBG into (1.10) gives a pressure sensitivity of −5.7 pm/MPa.

Figure 6:
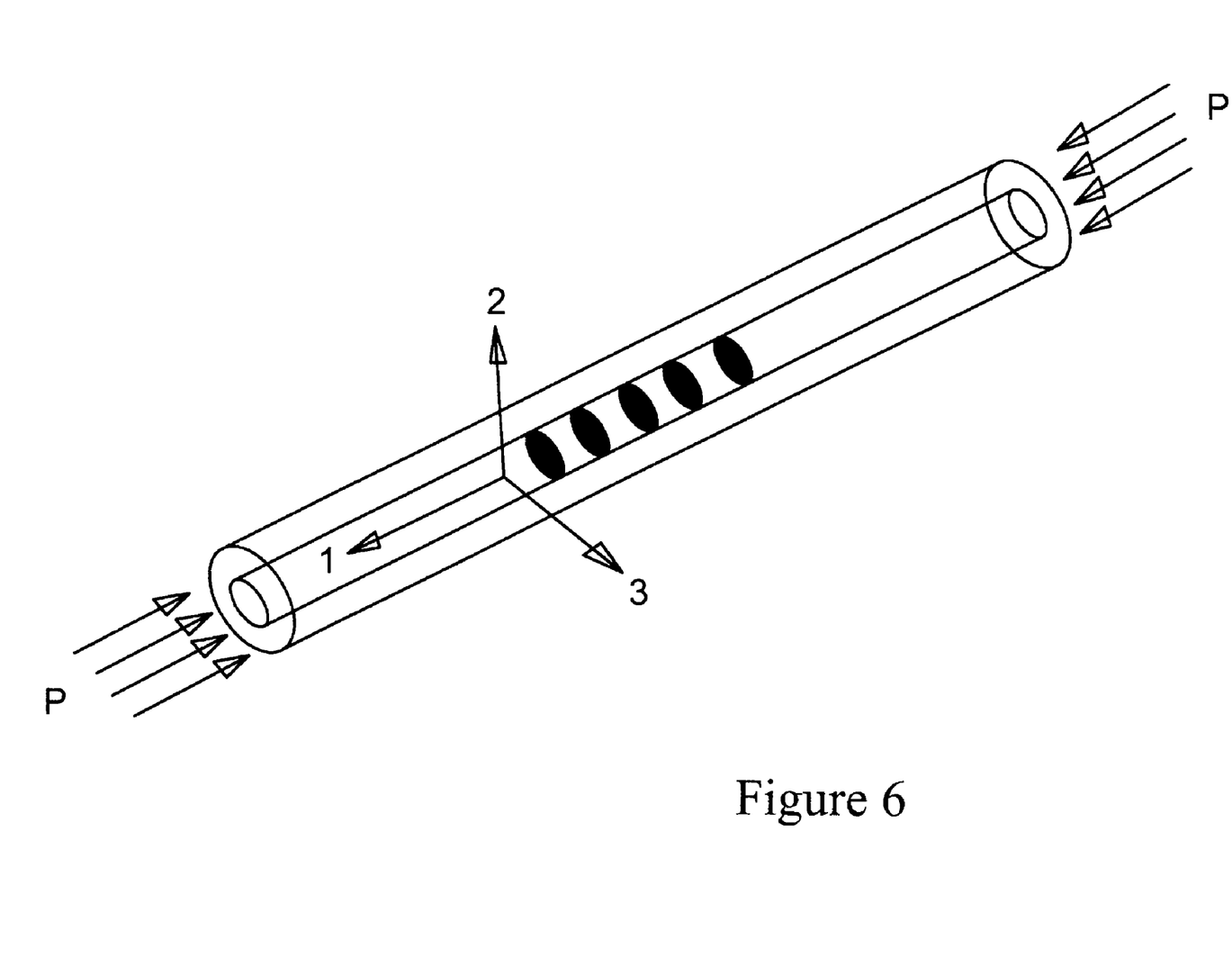
FIG. 6 shows load boundary conditions in accordance with the second embodiment.

Although it is possible to measure pressure using the scheme outlined above (i.e. three-dimensional hydrostatic pressure), this scheme does not give the best possible sensitivity to pressure. Inspection of (1.5) shows that the loading scheme that results in the most axial strain $\varepsilon_i$ will give the maximum possible sensitivity. The most efficient way to affect an axial strain on the geometry shown in FIG. 5 is to directly load the distal ends of the fibre, as shown in FIG. 6.

To calculate the sensitivity to pressure of this loading scheme, let us revert back to the strain vector, for this case the three-dimensional vector is:

$$\varepsilon_j = \begin{bmatrix} -1 \\ v \\ v \end{bmatrix} \frac{P}{E} \quad (1.11)$$

After substituting the strain vector into (1.5) we obtain:

$$\frac{\Delta\lambda_B}{\lambda_B} = -\frac{P}{E} - \frac{n_0^2}{2}\frac{P}{E}[p_{21} + p_{22}v + p_{23}v] \quad (1.12)$$

Re-arranging this for the sensitivity to pressure gives (1.13):

$$\frac{\Delta\lambda_B}{P} = -\frac{\lambda_B}{E}\left[1 - \frac{n_0^2}{2}(p_{12} - v(p_{11} + p_{12}))\right] \quad (1.13)$$

Evaluating this relation with typical material properties for FBGs gives the sensitivity to pressure of −17 pm/MPa. The theoretical sensitivity for this loading scheme is approximately greater than that for hydrostatic pressure.

The second embodiment of the sensor based on the load boundary conditions shown in FIG. 6 is as follows in Example 3.

Example 3

Figure 7:
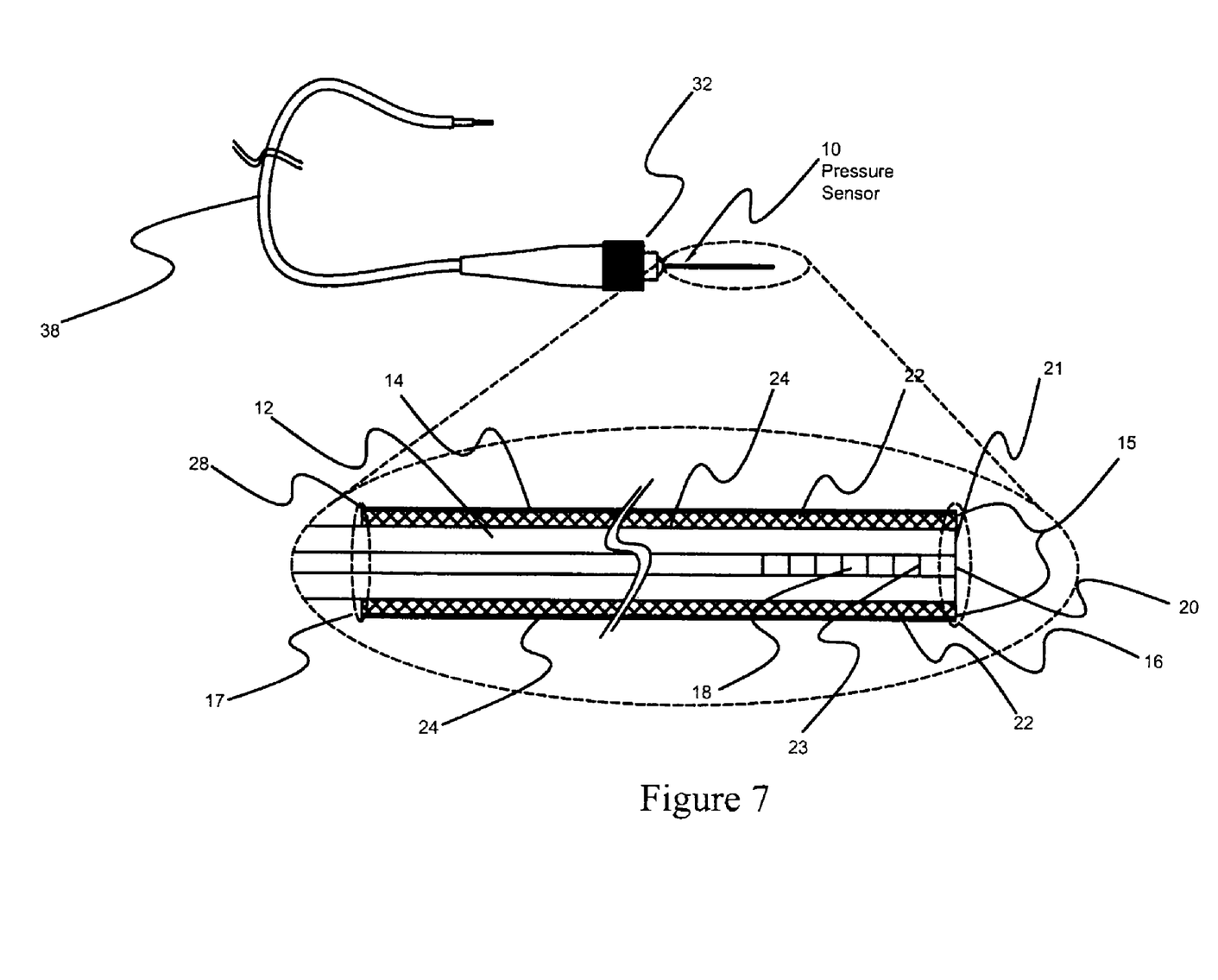
FIG. 7 is a longitudinal section of a pressure sensor in accordance with the second embodiment.
Figure 8:
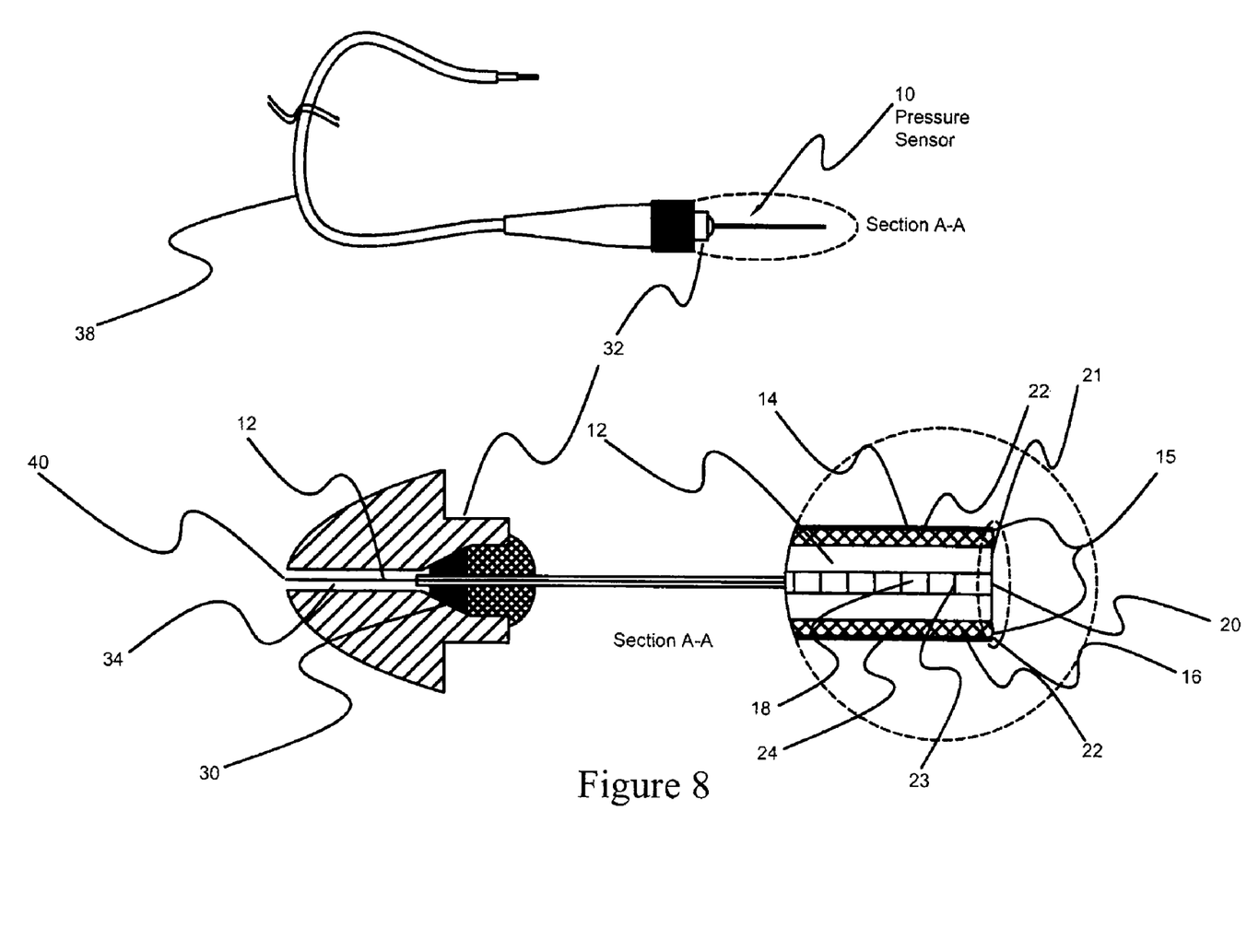
FIG. 8 is a close up of FIG. 7.

A pressure sensor, generally referred to as 10 is shown in FIG. 7. An optical fibre 12 is housed in a housing 14 having a bore 15 that terminates in a distal aperture 16 and a proximal aperture 17. The optical fibre has an in-fibre Bragg grating (FBG) 18 and a distal end 20 with a distal plane 21, preferably proximate to the distal aperture 16, and more preferably co-terminus with the distal aperture 16 as shown in FIG. 8. The housing 14 is preferably a hypodermic tube. The housing 14 is sized to accept both the optical fibre 12 and the FBG 18 and is selected from materials to protect the optical fibre 12 and FBG 18 from pressure on its circumferential surfaces 24 and to prevent undue bending of the optical fibre 12—in other words, it is selected to limit pressures on the FBG 18 to axial pressures arising from pressure exerted on the distal plane 21. The housing 12, in the present embodiment is hypodermic tubing. An annular seal 22 forms an impervious ring between the FBG and the housing 14. The annular seal 22 forms a seal at least at the FBG distal end 23. Again, this is to protect circumferential surfaces 24 of the FBG from fluid pressure. The annular seal 22 is a compliant material, such as silicone sealant, to allow axial strains to develop in the FBG 18 in response to pressure on the distal end 20. The proximal end 28 of the housing 14 is retained in a ferrule 30 that connects the housing 14 to a holder 32. The holder 32 functions as a strain reliever and has a holder bore 34 through which the optical fibre 12 passes freely from the proximal aperture 17 of the housing 14 into and through. The optical fibre 12 communicates with a detector by means of an optical patch cord 38 that is connected to a proximal end 40 of the optical fibre.

Example 4

Figure 9:
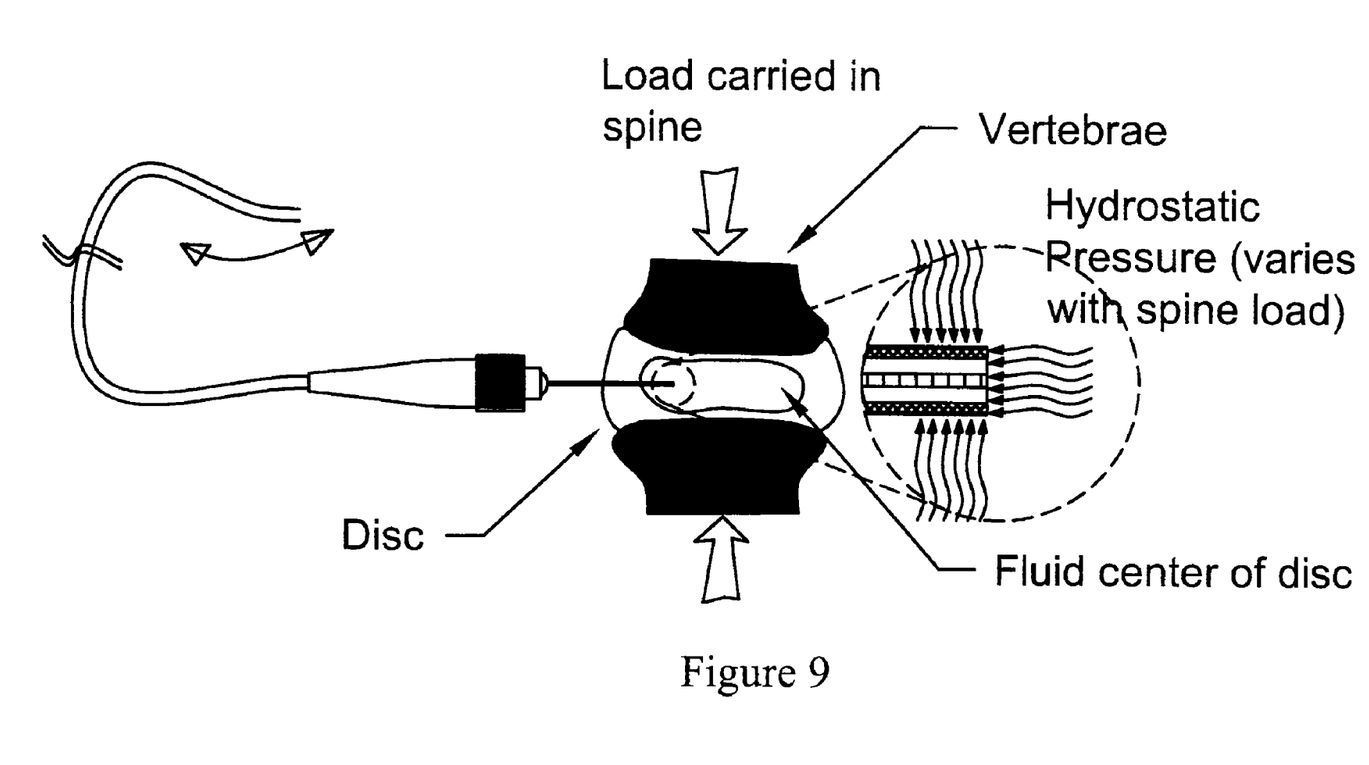
FIG. 9 shows a pressure sensor based on the second embodiment in an intervertebral disc.

FIG. 9 shows the pressure sensor inserted into an intervertebral disc. When compressive load is applied to the vertebrae of the spine, the center of the disc (the nucleus) responds with an increase in hydrostatic pressure. The magnitude of this pressure is believed to be a linear function with respect to the applied load.

The inset section view in FIG. 9 shows how pressure is applied to the pressure sensor when it is inserted into the disc. The pressure (shown by wavy arrows), that is applied to the housing produces little or no change in the reading given by the FBG because it produces little or no strain directly in the FBG. The housing and the silicone annular ring shield the FBG from pressure in this direction. The pressure applied to the distal end of the sensor, however, causes axial strains along the length of the FBG, and will therefore cause a change in the reading given by the FBG. With increasing compressive spine load, the pressure applied to the sensor end will increase, and so will the induced axial strain in the FBG. Therefore, one can calibrate the optical response of the FBG for pressure measurements. The housing also serves to provide some resistance to bending.

Figure 10:
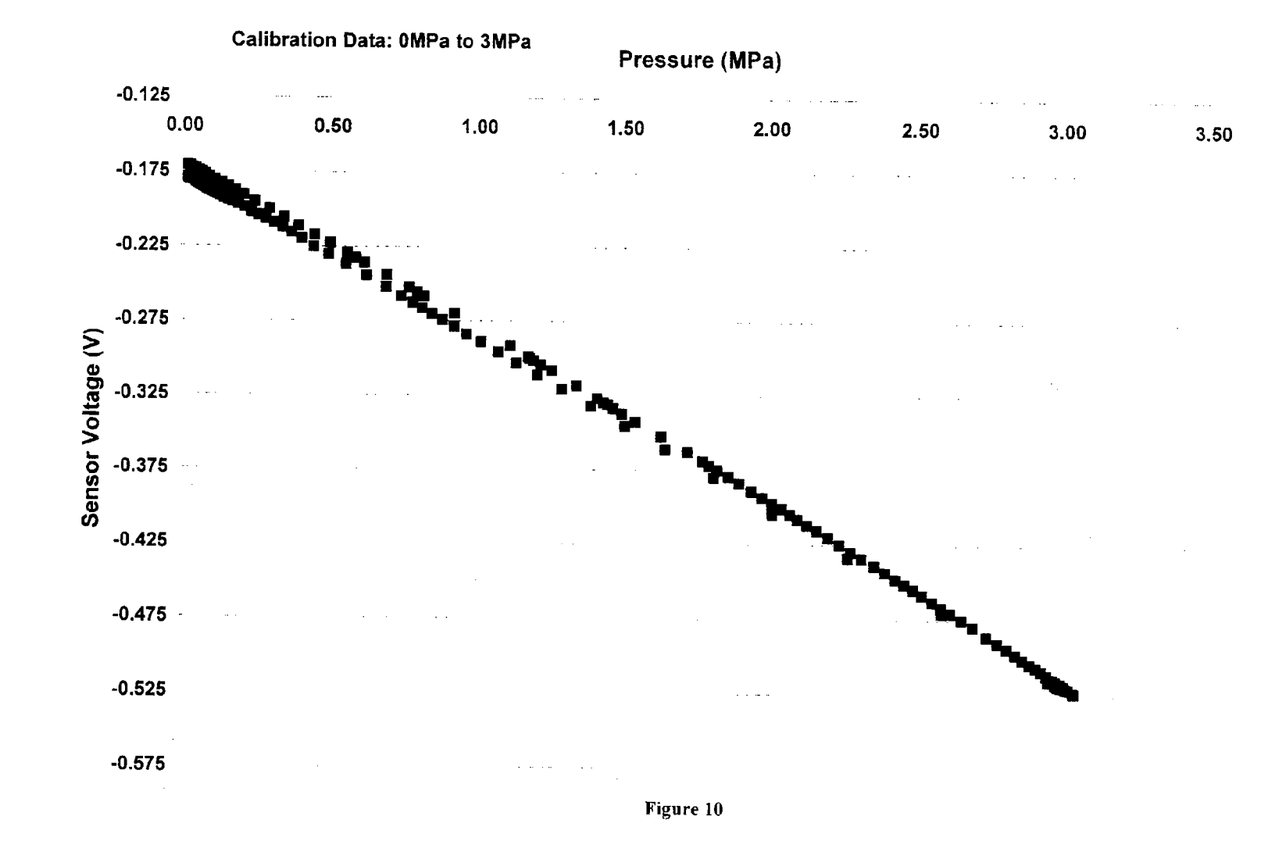
FIG. 10—output voltage versus pressure data taken from calibration of pressure sensor based on the second embodiment in a hydrostatic pressure test rig.

FIG. 10 shows the results of a hydrostatic pressure test for a 27 gage (0.4 mm outer diameter) FBG sensor. The maximum pressure applied to this sensor was 3 MPa. The coefficient of determination for a linear fit to the resulting data was 0.998.

Figure 11:
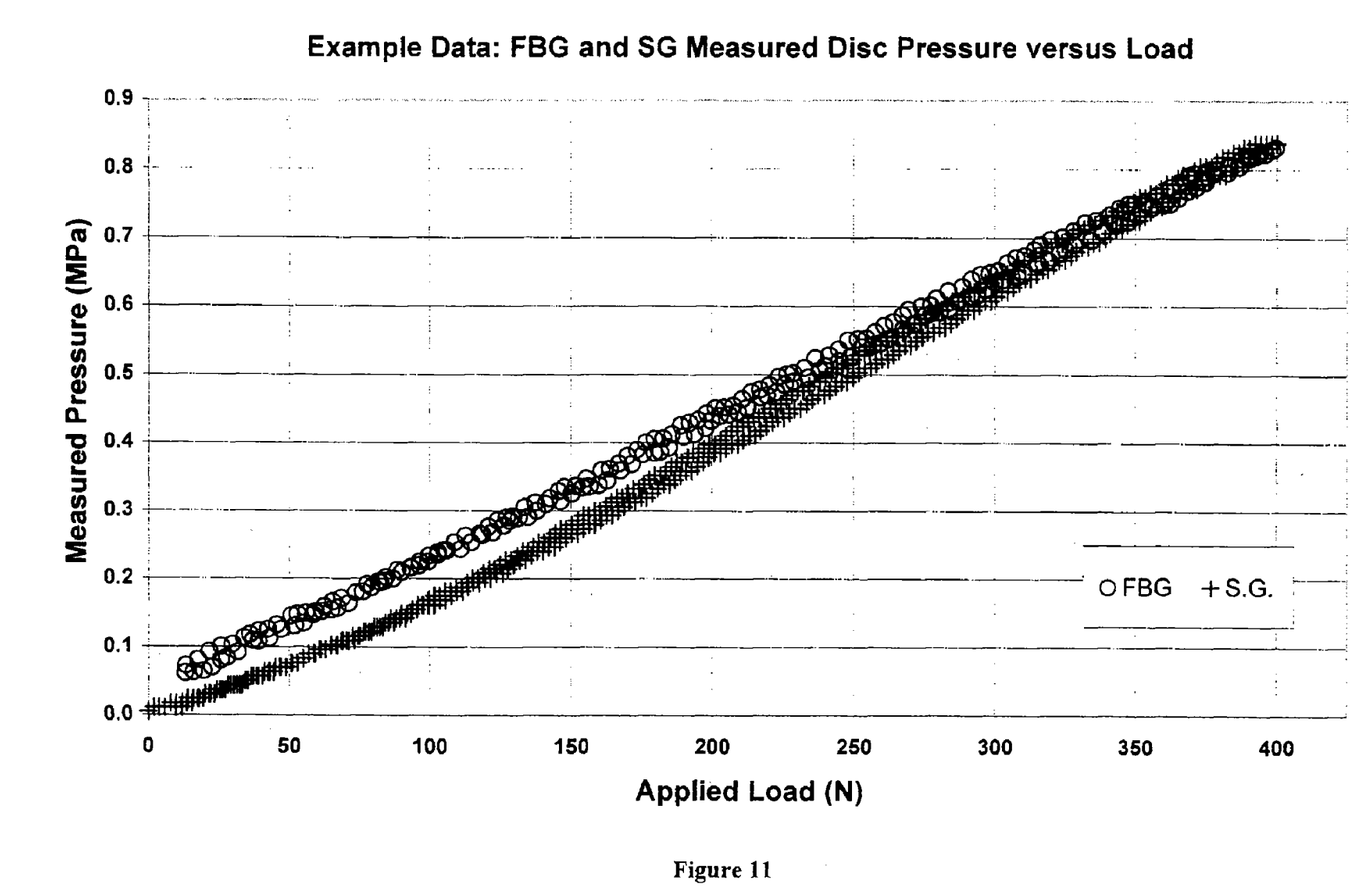
FIG. 11 shows results from 3 tests with a pressure sensor based on the second embodiment and 1 test with a ST pressure sensor in a bovine intervertebral disc.

FIG. 11 shows results obtained from three tests with the both the ST sensor (2.5 mm outer diameter) and the 21 gage (1.3 mm outer diameter) FBG sensor in a bovine disc.

Example 5

Human cartilage is a dual phase structure, including solid and liquid elements. Cartilage is present in all joints in the human body and is responsible for lubricating joints against wear and distributing loads. Without it, bone contact in joints would lead to premature joint degradation.

Some joints in the human body have cartilage that is deep enough to accommodate a FBG sensor. The knee and the hip joints in adults are examples.

Cartilage thickness varies, but is usually a few millimeters in large load bearing joints. FBG sensors will be embedded within cartilage. The small diameter of FBG sensor optical leads will not affect the range of motion of the joint.

When cartilage is loaded, the stress within it is approximately hydrostatic. Estimates of the physiological level for cartilage stress are on the order of a few MPa. As shown earlier, FBG sensors have the required resolution to make pressure measurements in this range. The intrinsic qualities of FBGs will allow novel pressure measurement schemes in joints that have previously not been attempted.

Methods for embedding FBG sensors in cartilage will be developed and tested. The first steps in this process will include extracting cartilage plugs from donor joints. Cartilage plugs will offer a simple geometry to work with, and will also allow for nominal pressure calculations and calibration. The contact mechanics between the FBG sensor and cartilage will also be addressed. Specifically, how the stress-strain behaviour of the host cartilage impacts the response of the FBG. Currently there is no ability to calibrate FBGs in structures with unknown Young's Modulus.

Example 6

Diagnosis of disc degeneration: As a disc degenerates, the nucleus pulposus can lose the ability to support load due to tears in the annulus which prevent the development of hydrostatic pressure in the nucleus pulposus or due to degeneration of the material of which the nucleus pulposus is comprised.

These changes to the disc will result in changes of the pressure response of the nucleus pulposus to load. Current imaging methods are not able to reliably assess mechanical changes in the disc. The FBG sensor will be used to measure pressure in the disc in vivo while the patient undergoes flexion and extension of the spine and in a range of other combinations of load and/or movement. The resulting pressure measurements will be interpreted to provide insight into the condition of disc and into mechanisms and mechanical triggers of disc degeneration.

Example 7

Provocative discography: The FBG sensor will result in an improved ability to identify surgical candidates based on characteristics of their intervertebral disc mechanics that will be revealed by measuring disc pressure with the FBG sensor while the patient undergoes various postures and exercises. This will be performed least invasively for patients who are scheduled to undergo provocative discography as a way to confirm that spinal surgery should be performed. Since some of these patients will be operated on and some not the FBG data will allow a more sensitive surgical threshold to be determined based on disc mechanics. In this sense the FBG sensor will become a "better discogram" and will incorporate dynamic information as FBG readings will be obtained with the patient moving. In discography the patient remains stationary.

Example 8

Magnetic resonance imaging: FBG sensors will be used to provide measurements of hydrostatic pressure, uniaxial and/or multiaxial strain, and temperature during or immediately before or after a magnetic resonance imaging (MRI) scan. Because MRI uses a strong magnetic field and radiofrequency waves, some metals can interfere with scans and transmission of electrical signals can be difficult. Because FBG sensors are non-metallic and non-electrical they will not be affected by and do not affect magnetic fields. They will therefore be used for a large range of applications in MRI scanning, such as linking changes in organ or tissue shape and size to changes in pressure or strain.

Example 9

Diagnosis of spinal stenosis: A FBG sensor of the bare fibre type will be inserted into the spinal canal in the manner of an epidural procedure. The sensor will be positioned between the cord and the bone in the spinal canal at successive levels in the spine and, at each location, pressure measurements will be made as the patient undergoes flexion and extension of the spine and for other combinations of load and movement. These pressures will be used to provide insight into the extent of the stenosis which exists or has occurred at each level.

Example 10

Characterization of spinal cord injury: In this application the FBG sensor will be used to obtain Cerebral Spinal Fluid (CSF) pressures before and after surgical decompression procedures. The FBG data will provide a measure of the efficacy of the decompression procedure. Measurement of CSF will also be useful to assess pressure changes related to spinal cord injury that may be useful in making decisions in the treatment of spinal cord injury patients.

Example 11

Diagnosis of Lumbar Instability: In patients with spinal instability, dynamic disc pressure measurements that will be taken with FBG sensors will identify new characteristics of pathologic instability. Since segmental instability is intimately associated with disc mechanics it is reasonable to expect that certain types of instability (i.e. spondylolisthesis vs. hyperflexion instability) will be associated with particular disc pressure signals as measured with the FBG sensor.

Example 12

Measuring pressure across a blood vessel blockage: In this application blood-pressure will be measured using the FBG sensor across a partial or complete blockage in an artery or vein. The FBG data will provide a measure of the degree to which blood flow is impeded because of the blockage. In the event that corrective procedures are used to clear the blockage, this method will also allow one to measure the degree to which the blockage has been corrected. Specifically, the pressure results from pre and post operative measurements will be compared.

Example 13

Inter-cranial pressure measurement and monitoring: In this application fluid pressure in the inter-cranial region between the brain and skull will be measured and monitored over time. When the inter-cranial pressure approaches or exceeds the blood pressure, blood will not diffuse into the brain and therefore the brain can become oxygen starved. Elevated inter-cranial pressure is commonly caused by brain swelling in response to trauma. Therefore, the inter-cranial pressure measurements will quantify the degree of swelling.

Example 14

Inter-compartmental muscle pressure measurement and monitoring: In this method pressure will be measured and monitored by inserting the sensor through the fascia of the muscle. When the compartmental pressure magnitude approaches or exceeds the blood pressure magnitude, blood diffusion into the muscle can be prevented.

The foregoing is a description of the preferred design of a pressure sensor. As would be known to one skilled in the art, variations that do not alter the scope of the technology are contemplated. For example, the housing can be of any inside diameter suitable to accept and protect the optical fibre, which for a FBG of 0.05 mm, is at least about 0.051 mm. For example, 0.2 mm inside diameter capillary tube, 0.4 mm inside diameter hypodermic tube, 1.2 mm inside diameter capillary tube or a 1.6 mm inside diameter capillary tubes are all contemplated. Future reductions in the diameter of the FBG would permit the use of still smaller diameter housing. The housing is preferably bio-compatible if the pressure sensor is to be used in bio-medical applications and can be any bio-medical tubing or similarly shaped article having a bore to accept the FBG and optical fibre, such as, for example, but not limited to, hypodermic tubing, hosing, a conduit or a sleeve composed of one or more of a polymer or polymers, co-polymers, glass, ceramic, Kevlar™ and metal. Also, two or more FBGs can be housed within the housing, allowing for measurement of pressure distributions or pressure differentials at a given time.

The invention claimed is:

1. A pressure sensor for connecting to a detector, said pressure sensor comprising:
   an optical fibre having a distal end with a distal plane for sensing pressure, a proximal end for communicating with a patch cord, and an in-fibre Bragg grating (FBG) situated proximate the distal end,
   a housing having a distal aperture, a proximal aperture and a bore therebetween, said housing sized to accept said optical fibre and said FBG, said FBG being housed in said housing and the housing configured so that the FBG is responsive to an axial component of a force produced by a fluid pressure at the distal end of the fiber and to attenuate coupling of radial components of the force to the FBG,
   an annular ring forming a flexible seal between said optical fibre and said housing at least distal to said FBG, and
   a holder configured to retain said housing, such that axial strain is transferred to said in-fibre Bragg grating housed within said housing by the fluid pressure at the distal end of the fiber.

2. The pressure sensor of claim 1 wherein said housing is bio-medical tubing.

3. The pressure sensor of claim 1, wherein the inside diameter of said housing is between 0.2 mm and 1.6 mm.

4. The pressure sensor of claim 1 wherein said FBG is defined in an optical fiber having a 0.125 mm outside diameter and said housing is 0.2 mm inside diameter.

5. The pressure sensor of claim 4 wherein said FBG is 10 mm in length.

6. The pressure sensor of claim 5 wherein said housing is a glass tube or a hypodermic tube.

7. The pressure sensor of claim 1 wherein said annular ring comprises silicone sealant.

8. The pressure sensor of claim 1 wherein said optical fibre and said housing are co-terminus at a distal end.

9. The pressure sensor of claim 1 further comprising at least two FBGs housed therebetween.

10. A method of measuring fluid pressure in a sample comprising inserting the pressure sensor of claim 1 into said sample, measuring an optical response, and comparing the optical response with a standard curve thereby measuring fluid pressure.

11. The method of claim 10 further comprising the step of calibrating said pressure sensor.

12. The method of claim 11 wherein said sample is a bio-medical sample.

13. The method of claim 12 wherein said bio-medical sample is an intervertebral disc.

14. A method of manufacturing a bio-medical pressure sensor comprising:
   selecting a biocompatible housing having a distal aperture, a proximal aperture and a bore therebetween,
   inserting an optical fibre comprising a FBG into said housing such that the FBG is within said housing,
   sealing the optical fibre to the biocompatible housing with a flexible annular ring at least distal to said FBG such that the housing attenuates coupling of radial components of a force associated with a fluid pressure at the distal aperture to the FBG, and
   inserting said housing into a holder to retain said housing and said optical fibre therein.

15. The method of claim 14 wherein said housing is bio-medical tubing.

16. The method of claim 14, wherein said housing has an inside diameter between 0.2 mm and 1.6 mm 17. The method of claim 14 wherein said FBG is 0.125 mm outside diameter and said housing is 0.2 mm inside diameter.

18. The method of claim 17 wherein said FBG is 10 mm in length.

19. The method of claim 18 wherein said housing is a glass tube or a hypodermic tube.

20. The method of claim 14 wherein said annular ring comprises silicone sealant.

21. The method of claim 14 wherein said optical fibre and said housing are co-terminus at a distal end.

* * * * *